US00PP21413P3

(12) United States Plant Patent
Tupy et al.

(10) Patent No.: US PP21,413 P3
(45) Date of Patent: Oct. 26, 2010

(54) COLUMNAR APPLE TREE NAMED 'GOLDLANE'

(50) Latin Name: *Malus domestica (Borkh.)*
Varietal Denomination: Goldlane

(75) Inventors: Jaroslav Tupy, Praha 6 (CS); Otto Louda, Pencin u Liberce (CS); Jan Zima, Turnov (CS)

(73) Assignee: Institute of Experimental Botany AS CR, v.v.i. (UEB), Praha (CS)

( * ) Notice: Subject to any disclaimer, the term of this patent is extended or adjusted under 35 U.S.C. 154(b) by 0 days.

(21) Appl. No.: 12/319,450

(22) Filed: Jan. 7, 2009

(65) Prior Publication Data

US 2010/0175157 P1 Jul. 8, 2010

(51) Int. Cl.
*A01H 5/00* (2006.01)

(52) U.S. Cl. ..... Plt./175
(58) Field of Classification Search ..... Plt./175, Plt./172
See application file for complete search history.

(56) References Cited

OTHER PUBLICATIONS

Upov-rom Plant Variety Database GTI Jouve Retrieval System 2009/05, Citation for *Malus* 'Goldlane', one page.*

* cited by examiner

*Primary Examiner*—June Hwu
(74) *Attorney, Agent, or Firm*—The Webb Law Firm

(57) ABSTRACT

A new and distinct *Malus domestics* (Borkh.) apple tree variety is provided which exhibits a columnar tree type, compact growth, predominant bearing on spurs and $V_f$-resistance against scab. The new variety yields late maturing, medium-sized, generally globose to obloid yellow-colored apple fruits having a firm and crispy flesh with very good eating and keeping qualities.

6 Drawing Sheets

Botanical classification: *Malus domestica* (Borkh.)
Varietal denomination: 'GOLDLANE'.

BACKGROUND OF THE INVENTION

The present invention comprises a new and distinct cultivar of apple tree botanically classified as *Malus domestica* (Borkh.) and known by the varietal name 'GOLDLANE'. The new variety is the result of a cross between 'UEB 3138/1' (female parent, unpatented) and 'Bohemia' (male parent, unpatented). The cross resulting in 'GOLDLANE' occurred in the Spring of 1998 at 310 meters above sea level with a mean annual temperature of 7.7° C. and a mean annual precipitation of 680 mm. The purpose of the breeding program was to develop late, dessert, disease resistant varieties with a columnar tree type. The new variety was discovered in the Fall of 2003 with the first fruiting of the original seedling in The Czech Republic. Subsequently, the new variety was asexually reproduced at the Institute of Experimental Botany AS CR, v.v.i., Station Strizovice, 45 Pencin u Liberce in The Czech Republic by budding/grafting on apple rootstocks in the Spring of 2004.

The new variety is similar to 'UEB 3138/1' as it is a columnar tree type and exhibits the presence of $V_f$-resistance against scab. However, 'GOLDLANE' exhibits larger sized fruits with a higher firmness and better keeping quality than 'UEB 3138/1'. The new variety is similar to 'Bohemia' in fruit size and fruit eating quality, but differs from its male parent, as 'Bohemia' is a ramified tree type and does not display the presence of $V_f$-resistance against scab. Further, the new variety has fruits that are yellow in color while its parents have predominantly red colored fruits. Additionally, the new variety is similar to apple tree variety 'Tuscan' (aka, Bolero) (U.S. Plant Pat. No. 6,225) in columnar tree type, fruit bearing mainly on spurs, medium sized fruit, and fruit shape with a short stem. However, the new variety differs from 'Tuscan' as it exhibits firm fruit flesh; the flesh of 'Tuscan' is soft. Further, 'Tuscan' has an orange skin overcolor on 20-25% of the fruit surface, while such an overcolor is absent on the present variety. Finally, 'Tuscan' does not exhibit the presence of $V_f$-resistance against scab. The following characteristics also distinguish the new variety from other varieties known to the breeders:

- Late, dessert-type, diploid variety;
- Columnar tree type;
- Trees exhibit medium vigor;
- The growth habit is compact and dense with very short internodes;
- Medium-sized fruits;
- Globose to obloid fruit shape;
- The fruit ground color is yellow with no overcolor;
- Short fruit stems;
- Very good eating and fruit keeping quality; and
- $V_f$-resistance against scab.

The new variety has been trial and field tested and has been found to retain its distinctive characteristics and remain true to type through successive asexual propagations.

DESCRIPTION OF THE DRAWINGS

The accompanying photographic drawings illustrate the new cultivar, with the color being as nearly true as is possible with color illustrations of this type. It should be noted that colors may vary with growing conditions and time of year:

FIG. 6 shows a close-up view of the fruits of the new variety at picking maturity.

DESCRIPTION OF THE PLANT

Figure 1:
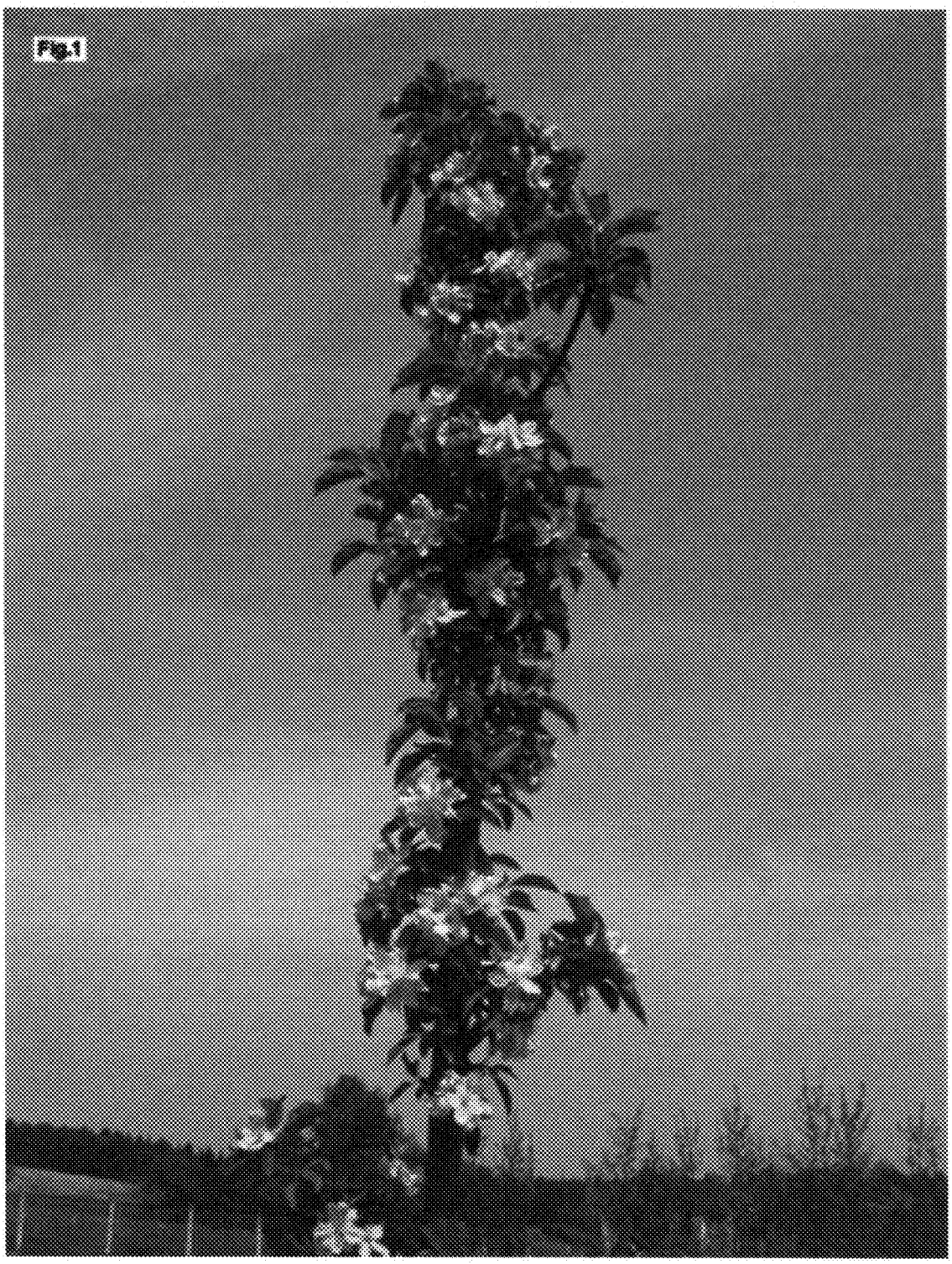
FIG. 1 is a photograph of the original tree of the new variety, showing canopy form at blossoming time.
Figure 2:
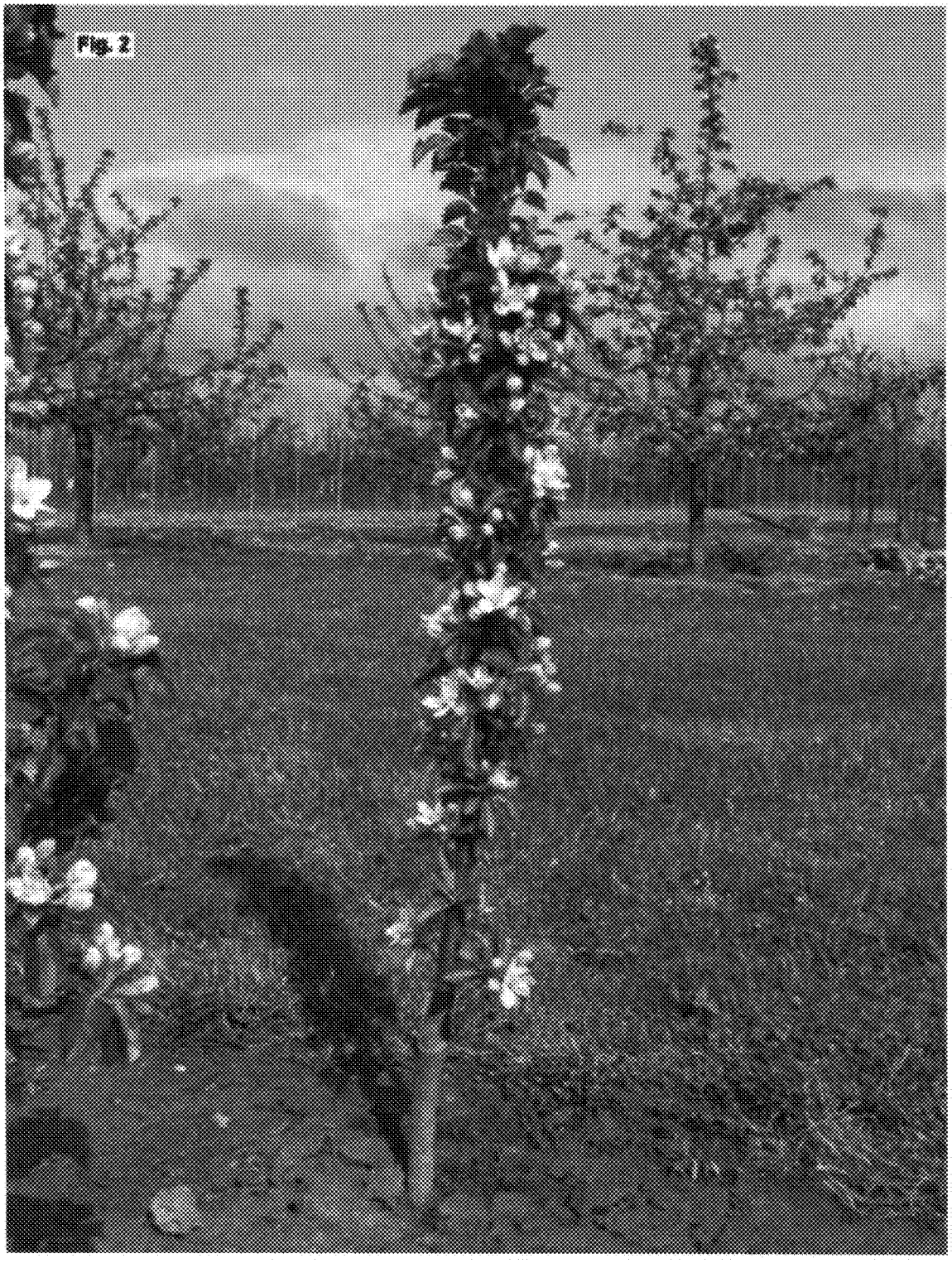
FIG. 2 shows a young, flowering tree of the new variety on MM 106 rootstock.
Figure 3:
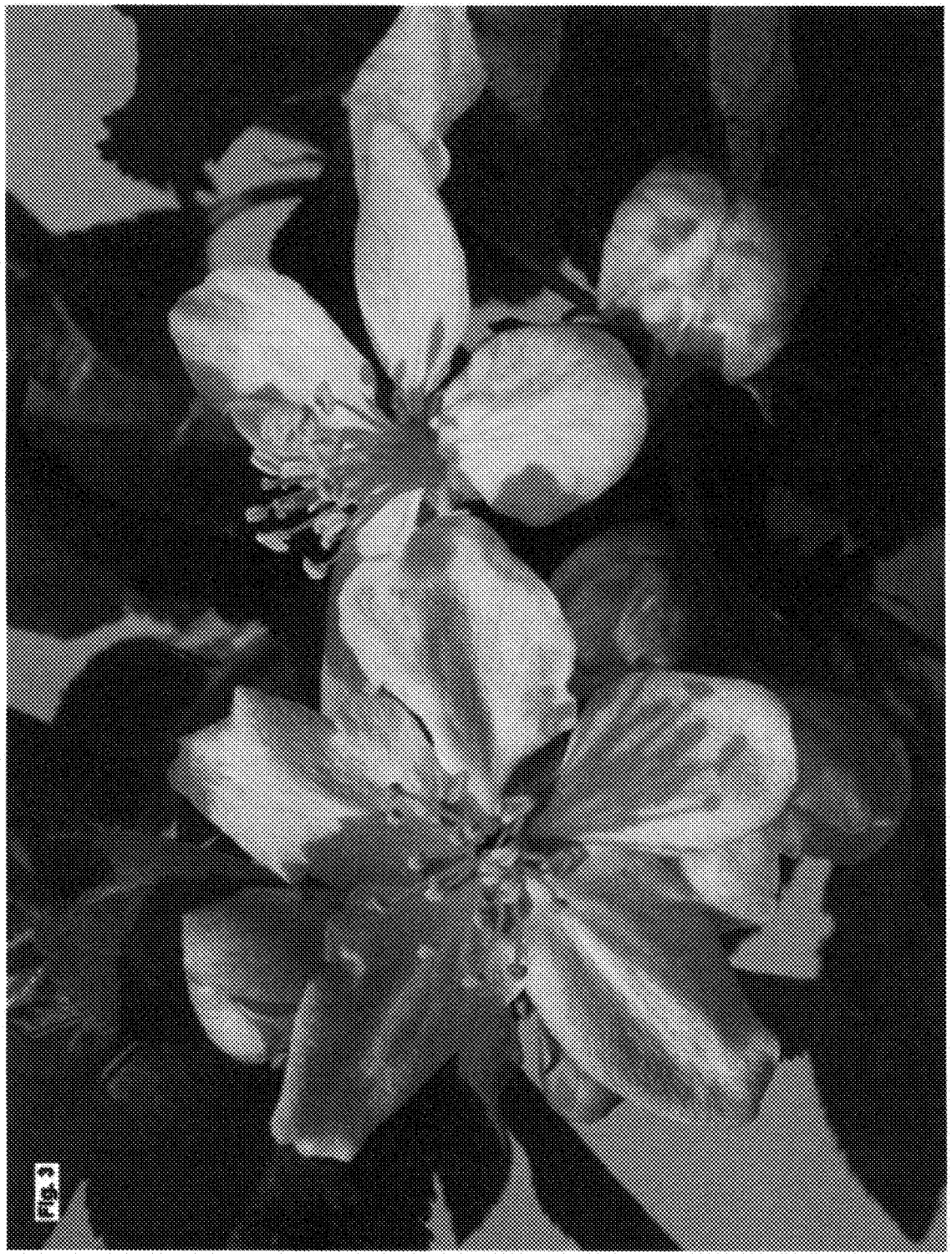
FIG. 3 shows the blossoms of the new variety.
Figure 4:
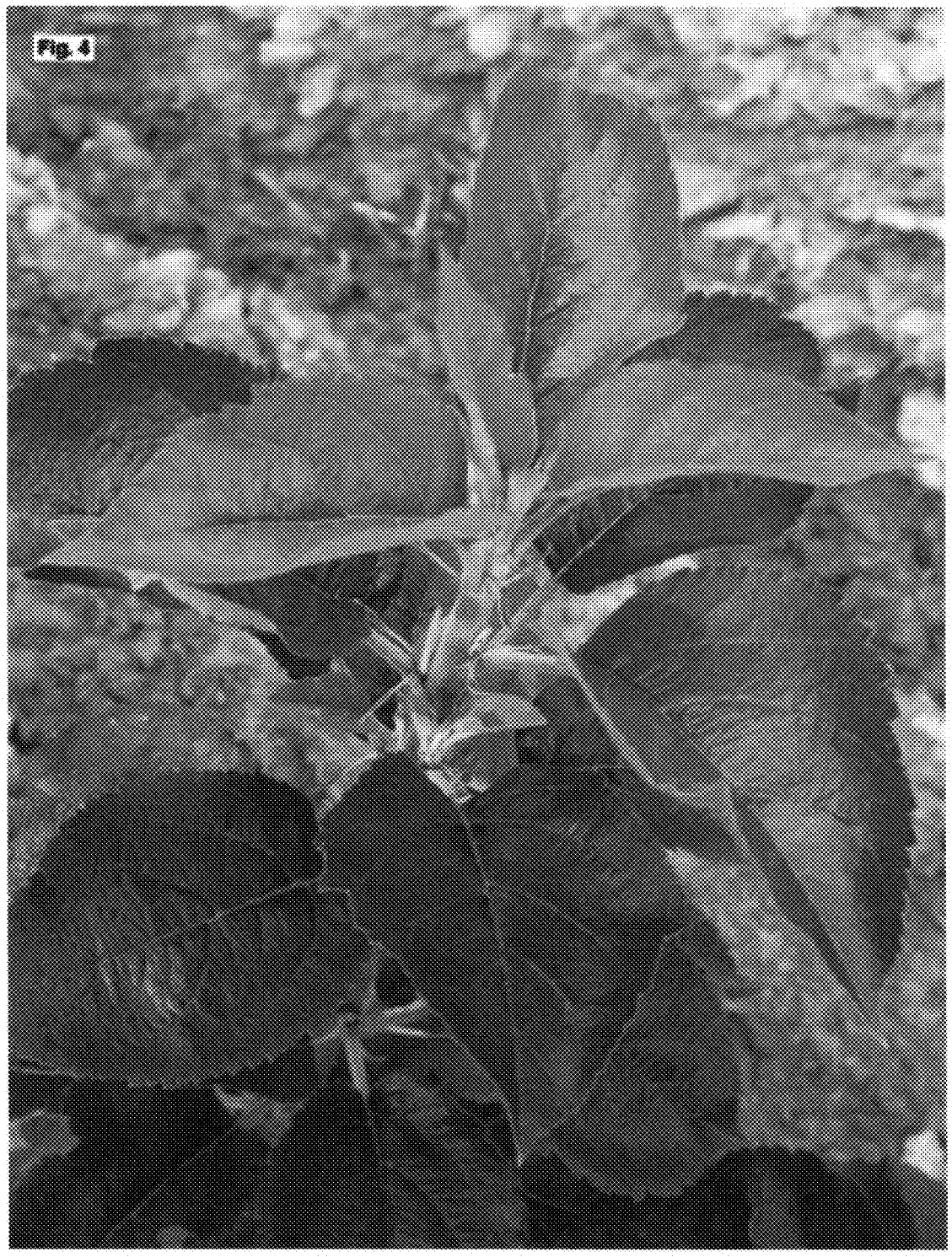
FIG. 4 shows a growing shoot of the new variety.
Figure 5:
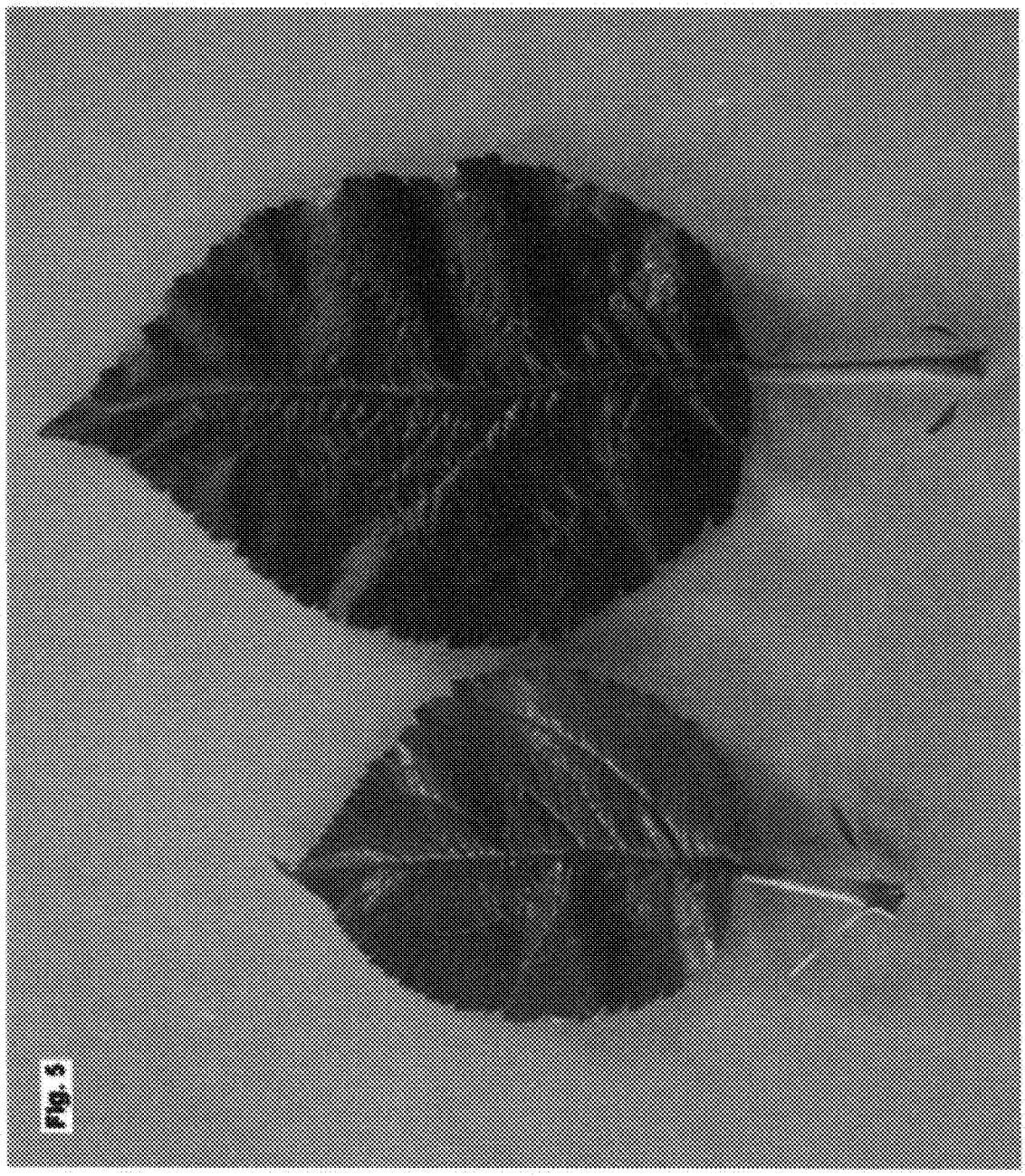
FIG. 5 shows a close-up view of the young and mature leaves of the new variety.
Figure 10:
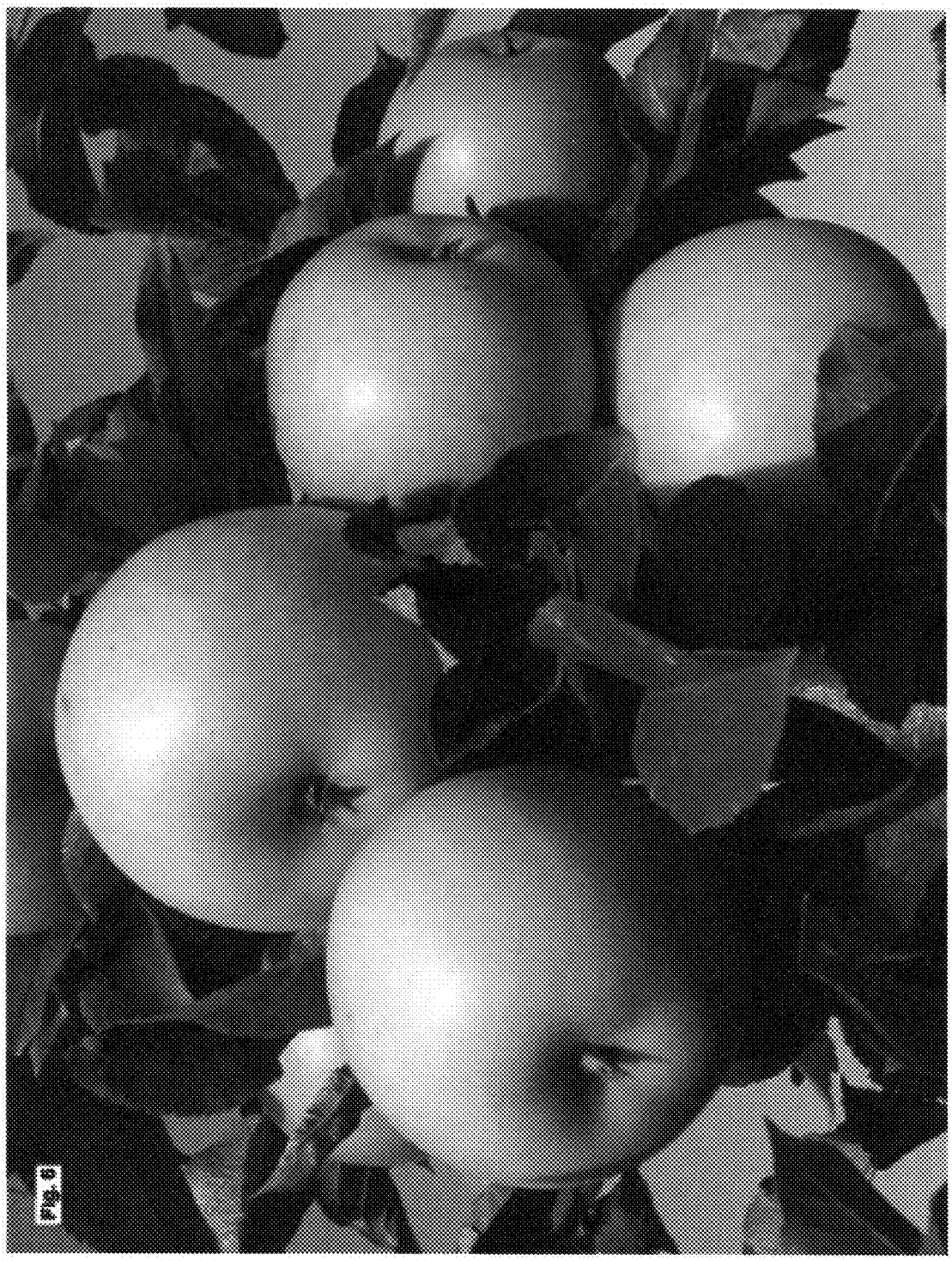

The following detailed description sets forth the characteristics of the new cultivar. The new variety was grown under natural field conditions in The Czech Republic. The growing area is 310 m above sea level with a mean annual temperature of 7.7° C. and a mean annual precipitation of 680 mm. The following fertilizer combination was used (Kg/ha/year): 55 parts nitrogen, 25 parts phosphorous, 60 parts potassium, 55 parts calcium, and 5 parts magnesium. Color references are primarily to The R.H.S. Colour Chart of The Royal Horticultural Society of London and were identified under natural light.

TREE

Age: 9 years from sowing.
Size: 3.4 m high, 0.6 m wide.
Vigor: Medium.
Density: Thick.
Form: Erect and compact; free of conventional side branches.
Production: Very precocious.
Growth Type: Columnar
Bearing: Mainly on spurs.
Trunk:
- *Size.*—Approximately 10 cm in diameter at 30 cm from the soil line.
- *Surface texture.*—Smooth.
- *Bark color.*—177B.
- *Lenticels* (100 *cm above ground*).—Length.—4 mm to 6 mm. Width: 0.5 mm to 1 mm. Color: 159D. Density: Approximately 8 lenticels per 1 $cm^2$.

Branches:
- *Overall description.*—A conventional branching system along the tree trunk is lacking.
- *Diameter.*—Very small.
- *Surface texture.*—Smooth.
- *Color.*—166A.
- *Form.*—Straight.
- *Average crotch angle.*—About 45 degrees.
- *Bud arrangement.*—Alternate. Internode length: 1.6 cm. Lenticels (on 1 year shoot): Length: 0.5 mm. Width: 0.5 mm. Shape: Round. Density: Variable, with a mean of 10 lenticels per 1 $cm^2$. Color: 159C.

Leaves (measured at the middle of growing shoot):
- *Length.*—About 100 mm to about 120 mm, averaging 109 mm.
- *Width.*—About 60 mm to about 80 mm, averaging about 65 mm.
- *Form.*—Elliptical to oval.
- *Texture.*—Smooth.
- *Thickness.*—Moderately thick.
- *Base.*—Varies between asymmetric and symmetric.
- *Apex.*—Mostly straight; acute.
- *Margin.*—Biserrate.
- *Pubescence.*—Upper surface: None present. Lower surface: Fine on veins.
- *Color.*—Young leaves: Upper surface: 144A. Lower surface: 144B. Mature leaves: Upper surface: 147A. Lower surface: 147C.
- *Stipules.*—Average number: 2. Arrangement: Opposite. Length: About 11 mm. Width: About 2 mm. Color: 147B.
- *Petiole.*—Shape: Straight with thickening and flattening at the base. Length: About 32 mm to about 50 mm, averaging about 40 mm. Diameter: 2 mm to 3 mm in the middle. Color: 144C with slight 59C at the base.
- *Veins.*—Venation type: Net-like, medium dense. Color: Upper surface: 144D. Lower surface: 145C.

Flower buds:
- *Pedicel.*—Length: Typically in the range of 11-16 mm, with an average of 14.5 mm. Diameter: 1.8 mm on average. Color: 144B.
- *Bud.*—Length: 16.5 mm on average. Width: 13 mm on average. Color: 63B.

Flowers:
- *Bloom timing.*—Early to medium 2 to 3 days before 'Golden Delicious'.
- *Blooming period.*—Medium; about 7 days and depends on weather conditions.
- *Pollination requirements.*—Diploid, self-sterile, needs good pollinators such as the common scab-resistant pollinator *Malus* (Crab Apple) 'Evereste'.
- *Number of flowers per cluster:* 6, rarely 5.
- *Fragrance.*—Faint.
- *Petals.*—Number: 5. Length: 21.9 mm on average. Width: 14.7 mm on average. Shape: Ovate. Aspect: Positioned free to overlapping. Margin: Entire. Texture and appearance: Soft and smooth.
- *Color.*—When opening: Upper surface: 155D and 65A to 65B. Lower surface: 155D and 63C. Fully opened: Upper surface: 155C and 65C to 65D. Lower surface: 155D and 64D to 65A.
- *Sepals.*—Shape: Elongated and conical; pointed. Margin: Entire. Texture: Upper surface: Finely pubescent. Lower surface: Pubescence present. Length: 8 mm on average. Width: 3 mm on average. Color: Upper surface: 145B, tip 59B. Lower surface: 144B, tip 59B.
- *Stamens.*—Number (per flower): 19 to 20. Filament length: 6-10 mm.
- *Anthers.*—Shape: Oval. Length: 2 mm. Color: 10B.
- *Pollen.*—Color: 12B. Amount (generally): Medium to high.
- *Pistils.*—Number: 1 pistil with 5 styles fused at the base. Length: 15.5 mm on average.
- *Style.*—Length: 11 mm on average. Color: 145A. Stigma: Shape: Rounded. Color: 151B.

Fruit:
- *Maturity when described.*—Eating maturity — after 3 months in common storage.
- *Date of picking.*—Oct. 17, 2006.
- *Size.*—Axial diameter: Average of 60 mm. Transverse diameter: Average of 76 mm.
- *Form.*—Globose to obloid.
- *Cavity.*—Shape: Funnel-shaped with medium russetting. Depth: Average of 14 mm. Breadth: Average of 33 mm.
- *Basin.*—Shape: Saucer-shaped and smooth with weak irregular ribbing. Depth: Average of 6 mm. Width: Average of 24 mm.
- *Calyx.*—Persistent with semi-erect lobes; absent to weak crowning at the calyx end of the fruit.

Skin:

*Thickness.*—Medium.

*Texture.*—Smooth, free of russet.

*Tendency to crack.*—Absent.

*Color.*—Overcolor absent.

*Ground color.*—13A; with lenticels scarce and so small they are almost invisible.

*Bloom or greasiness.*—Absent.

Flesh:

*Aroma.*—Medium.

*Color.*—14D.

*Texture.*—Firm, crisp, and fine-grained.

*Eating quality.*—Very good, rich flavor with a harmonic sugar to acid ratio.

Core:

*Bundle area.*—On longitudinal section-defined with vascular strands as onion shaped, width 35 mm, height 24 mm, core locules moderately open.

*Bundle.*—Vascular strands medium distinct.

*Calyx tube.*—Narrow and funnel-shaped.

*Depth of tube to shoulder.*—15 mm (calyx tube itself).

*Styles.*—Persistent as dry residues.

*Stamens.*—Persistent as dry residues.

*Seed cells.*—Wall: Smooth. Depth: 14 mm. Breadth: 5 mm. Longitudinal section: About 22 mm (length of seed cell).

Seeds:

*Number perfect.*—10.

*Number in one cell.*—2.

*Length.*—9 mm.

*Breadth.*—About 4 mm.

*Form.*—Long and conical with an acute tip.

*Color.*—166A to 177A.

Stem:

*Length.*—Typically between 15 and 20 mm; average of 17 mm.

*Width.*—2 mm on average.

*Color.*—144B and 200C.

Fruit characteristics:

*Percent soluble solids.*—13.8 Brix.

*Titratable acidity.*—7.86 g/l.

*Penetrometer reading.*—6.2 kg/cm$^2$.

Use: Late dessert variety with a columnar tree type having very good eating quality and long storage capacity that is primarily suitable for home gardens.

Shipping quality: Good.

Keeping quality: Very good, almost 6 months in common storage.

Tree winter hardiness: No frost damage observed at the place of origin, lowest winter temperatures approximately −20° C.

Bud winter hardiness: No frost damage observed at the place of origin, lowest winter temperatures approximately −20° C.

Drought tolerance: Unknown.

Disease resistance: $V_f$-resistance against scab; mildew tolerance observed.

Pest resistance/susceptibility: None observed.

I claim:

1. A new and distinct variety of *Malus domestica* (Borkh.) apple tree substantially as is herein described and illustrated.

* * * * *